United States Patent [19]
Barnwell et al.

[11] Patent Number: 6,153,218
[45] Date of Patent: *Nov. 28, 2000

[54] BIPHASIC CAPSULE FORMULATION

[75] Inventors: Stephen George Barnwell, Chester; Simon Higginbottom, Little Sutton; Ian Peter Whelan, Carlisle; Stephen John Burns, Oakwood, all of United Kingdom

[73] Assignee: Provalis UK Limited, United Kingdom

[ * ] Notice: This patent issued on a continued prosecution application filed under 37 CFR 1.53(d), and is subject to the twenty year patent term provisions of 35 U.S.C. 154(a)(2).

[21] Appl. No.: 08/666,563

[22] PCT Filed: Dec. 12, 1994

[86] PCT No.: PCT/GB94/02703

§ 371 Date: Jun. 13, 1996

§ 102(e) Date: Jun. 13, 1996

[87] PCT Pub. No.: WO95/16438

PCT Pub. Date: Jun. 22, 1995

[30] Foreign Application Priority Data

Dec. 13, 1993 [GB] United Kingdom .................... 9325445

[51] Int. Cl.[7] ................. A61K 9/48; A61K 9/64
[52] U.S. Cl. ............................ 424/451; 424/456
[58] Field of Search ..................... 424/451, 453, 424/456, 463, 464

[56] References Cited

U.S. PATENT DOCUMENTS

| 4,894,978 | 1/1990 | Schönmann et al. ............ 53/560 |
| 5,387,421 | 2/1995 | Amidon et al. ................ 424/472 |

FOREIGN PATENT DOCUMENTS

| 0 211 079 | 2/1987 | European Pat. Off. . |
| 0 255 002 | 2/1988 | European Pat. Off. . |
| 0 308 637 | 3/1989 | France . |
| 39 24 887 | 4/1990 | Germany . |
| 90/12583 | 11/1990 | WIPO . |
| 92/06680 | 4/1992 | WIPO . |

*Primary Examiner*—Thurman K. Page
*Assistant Examiner*—Susan Tran
*Attorney, Agent, or Firm*—Pennie & Edmonds LLP

[57] ABSTRACT

Capsule formulations are provided containing at least two different fill compositions which are prevented from mixing either by providing both of the fill compositions as solids or by providing a physical barrier which separates the fill compositions so that they are prevented from mixing. The invention has the advantage that two different formulations can be provided in a single capsule without one of the formulations having an adverse effect on the other.

14 Claims, No Drawings

BIPHASIC CAPSULE FORMULATION

FIELD OF THE INVENTION

The present invention relates to improved capsule formulations, in particular biphasic capsule formulations.

BACKGROUND OF THE INVENTION

WO-A-9206680 discloses biphasic release formulations for lipophilic drugs comprising a $C_{12}$–$C_{24}$ fatty acid and a pharmaceutically active substance. A portion of the formulation is formulated for non-sustained release and is generally in liquid form and a portion is formulated for sustained release on non-parenteral administration and will generally be a solid.

The formulations are extremely effective for the administration of lipophilic pharmaceutically active substances greatly enhancing oral bioavailibility of propranolol. These results have been published (Barnwell et al, *J. Controlled Release*, 28, 306–309 (1994)), but it has been discovered that there are certain problems with the stability of the compositions even when stored at ambient temperature.

After capsules containing biphasic formulations such as those described in WO-A-9206680 have been stored for periods of greater than 3 months at ambient temperature, there is a decline in in vitro dissolution performance compared with initial values. The level of propranolol released from the formulation after 12 months' storage at ambient temperature was found to be reduced by 50% compared with initial values. In contrast, prolonged storage of capsules containing only the liquid rapid-release phase and capsules containing only the solid sustained release phase did not result in any change in dissolution profile. This unstable release profile is therefore a problem only with biphasic formulations and represents a serious drawback in the development of such formulations since, clearly, a pharmaceutical formulation which is not stable under ambient storage conditions is of limited use in practice.

On investigation, it appeared that the deterioration in the release profile had arisen because, unexpectedly, the two phases of the formulation had become mixed during the storage of the capsules and the mixing of the phases had caused the release characteristics of both parts of the formulation to deteriorate. Deterioration was characterised by a visible intermixing between the two phases and a decline in in vitro dissolution performance. The rate of intermixing between the liquid rapid and solid sustained-release phases of the formulation was accelerated at elevated storage temperatures, eg 37° C., but much reduced at 4° C.

SUMMARY OF THE INVENTION

Therefore, in a first aspect of the invention there is provided a pharmaceutical formulation comprising a capsule containing at least two fill compositions, characterised in that the compositions are prevented from mixing with one another.

DETAILED DESCRIPTION OF THE INVENTION

The capsule fill compositions may be compositions comprising $C_{12}$–$C_{24}$ fatty acids such as those disclosed in WO-A-9206680. The invention is particularly useful when one of the fill compositions is a solid and one a liquid, especially when the solid component also comprises glycerides, for example the GELUCIRE™ mixture disclosed in Example 1 of WO-A-9206680. In that case, the fatty acids tend to dissolve the lower molecular weight lipids of the solid composition so that they gradually mix with the liquid composition. The progressive solubilisation of the lower molecular weight glycerides into the liquid composition slows down the rapid release characteristics of the liquid phase. It also leaves in the solid phase only the higher molecular weight glyceride components which do not easily erode to allow the release of the remaining fatty acid and the active material. An example of a modified capsule would be an adaptation of the potato starch Capill® capsules manufactured by Capsugel Limited. In this case, the starch capsule would be manufactured with a central partition and two open ends. This would allow two separate formulation components to be filled, each end of the capsule being sealed by the usual potato starch cap. Thus the sustained release of the active material from the solid component is retarded. These changes in drug release may be monitored using an in vitro dissolution method such as that described in Example 2 below.

However, there may be other reasons for wishing to separate the two fill compositions, for example they may contain different active compounds or different excipients which interact in an unfavourable manner and therefore the present invention is not limited to compositions such as those described in WO-A-9206680.

For example, with compositions such as those disclosed in GB Application No 9417524.7 there is the possibility of unfavourable interaction of the active ingredient, particularly if it is a protein, and the pH modifying agent (for instance, carbonate or bicarbonate). Thus, the present invention is particularly useful for such formulations.

The simplest method of preventing phase mixing is to formulate both of the fill compositions as solids but of course this will not be possible in all cases. Therefore, it is often desirable to provide some sort of physical barrier within the capsule to prevent mixing of the fill compositions.

However, there are problems with this approach. One problem is that the placing of a physical barrier between two compositions in a capsule often leads to the collapse of the capsule walls and any barrier which has this effect is of no use whatever.

Secondly, it is important to ensure that any material used as a physical barrier between fill compositions in a capsule does not interact with the fill compositions themselves. One solution which may overcome this problem is to provide a barrier of the same material as the capsule. This may be achieved by manufacturing capsules having two compartments and will be particularly effective for hard gelatin capsules and starch capsules.

In some cases, it will not be possible to manufacture the barrier from the same material as the capsule shell. There may be a variety of reasons for this, for example the difficulties in manufacturing a two-compartment capsule and the weakness in the capsule wall which a central barrier within the capsule may introduce. In addition, for soft gelatin capsules, the capsule walls may not be strong enough to support a central barrier in the capsule.

In such cases a barrier must be introduced into the capsule after manufacture and this will usually be done as the capsule is filled. This will retain the advantage of low manufacturing cost of the capsules whilst still separating the fill compositions and preventing them from mixing.

The choice of material for the barrier is important and several factors must be taken into account. For example, if hydrophobic fill compositions are used, it may be desirable to use a hydrophilic material as a barrier between the fill compositions. On the other hand, if the fill compositions are hydrophilic in nature, then a hydrophobic material will be more suitable.

It is also highly desirable that the material used as a barrier should have a melting point such that it is a solid at any likely storage temperature. Therefore, the melting point should, at the least, be higher than 25° C. (room temperature) but it is much preferred that the material should not begin to melt until it reaches about 37° C. (body temperature).

A barrier formed from such a material has the advantage of easy formation since the barrier material can simply be filled into the capsules in a molten state at a temperature above its melting point and then allowed to cool and form a solid barrier. The barrier material will be added to the capsule after the first fill composition has been put into the capsule but before the addition of the second fill composition so as to form an effective barrier between the two compositions.

If the capsule is required to contain more than two fill compositions then layers of the barrier material can be added to the capsule between additions of the different fill compositions.

In addition, the barrier material must, of course, be physiologically compatible since it is to be included in a pharmaceutical formulation.

Materials which have been found to be particularly useful as barrier materials in capsules are glycerides having a transition temperature (melting point) above 37° C. Suitable glycerides include di- and tri-glycerides, such as many of the various GELUCIRE compounds, which are hydrogenated fatty acid esters available from Gattefosse. (The word GELUCIRE is a trade mark.) Other trade marks of suitable glycerides include LABRAFIL and PRECIROL. GELUCIRE compounds and other suitable compounds having transition temperatures of from 40° C. to 70° C. are preferred. Specific examples of exemplary GELUCIRE compounds, and their equivalents include:

GELUCIRE 44/14
GELUCIRE 50/02
GELUCIRE 50/13
GELUCIRE 54/02 (also available as PRECIROL)
GELUCIRE 62/05 and
GELUCIRE 64/02 (also available as PRECIROL WL 2155).

(The first two digits in the numeric portion of the GELUCIRE name represent the liquid/solid phase transition temperature in degrees centigrade and the second two digits represent the hydrophile/lipophile balance (HLB) value.

GELUCIRE 44/14 has a high HLB value and is therefore relatively hydrophilic. This means that it is particularly useful as a barrier in capsules containing lipophilic fill compositions such as those described in WO-A-9206680 since it will be immiscible with both of the fill compositions.

The other compounds are more suitable for use in capsules with a hydrophilic fill since they are all relatively lipophilic.

A further use for the hydrophilic phase barrier may be to allow the formulation of a hydrophilic drug for co-administration with the lipophilic delivery system described in WO-A-9206680. An example of this application is the formulation and delivery of a non-membrane damaging bile acid (a hydrophilic material) as described in WO-A-9325192 together with a lipophilic drug in the lipophilic delivery system described in WO-A-9206680. The advantage of this arrangement is for the improved delivery of drugs which undergo both high hepatic first-pass metabolism and enterohepatic recycling (e.g. haloperidol, chlorpromazine and morphine) or where the non-membrane damaging bile acid can attenuate the toxic effects of a drug subject to high first-pass metabolism and formulated as described in WO-A-9206680.

Conversely, where a lipophilic barrier is used to separate hydrophilic phases it may act as a reservoir for a co-administered lipophilic drug.

Another way in which intermixing may be prevented with the biphasic rapid and sustained-release formulations described in WO-A-9206680 containing $C_{12}$ to $C_{24}$ fatty acids, is to ensure that the rapid-release phase remains a solid at normal storage temperature, e.g. below 30° C. This may be achieved by mixing a hydrophobic Gelucire® with a melting point above 30° C., exemplified by Gelucire 33/01, with the molten rapid release component before filling into capsules, the rapid-release phase solidifying on cooling and thus being unable to undergo mixing with the resident solid sustained-release formulation component. An example of this formulation approach is given below in Example 3.

It is preferred that hard gelatin capsules are used and, in that case, liquid fill compositions may contain gelatin softening agents such as those described in WO-A-9102520. Suitable gelatin softening agents can be found by reference to the art of manufacturing soft gelatin capsules where such materials are incorporated into the mix which forms the gelatin wall. Particularly suitable gelatin softening agents include glycerol, propylene glycol, glycerol mono-oleate and sorbitol.

The capsules may be enteric coated or otherwise protected to ensure better survival of the pharmaceutically active compound through the stomach. Any convenient enteric protection method may be used. Capsules containing the formulation may be coated with an enteric coat such as hydroxypropylmethylcellulose phthalate or by the commercial coating process of Pharma-Vinci A/S (Denmark).

The formulations of the invention may be prepared by any suitable process but when a solid barrier material is used then the process may comprise filling the first fill composition, the barrier material and the second fill composition sequentially into a suitable capsule.

Therefore, in a further aspect of the invention, there is provided a process for the preparation of a capsule containing at least two fill compositions separated by a barrier material, the process comprising filling a first fill composition, the barrier material and a second fill composition sequentially into a suitable capsule.

Preferred barrier materials are as described above.

The capsule may be of any suitable material, for example hard gelatin capsules, soft gelatin capsules and starch capsules but gelatin capsules are preferred, particularly hard gelatin capsules.

EXAMPLES

The invention will now be further described with reference to the following examples which are not intended to be limiting.

Example 1

Biphasic Propranolol Formulation with Phase Barrier

The following example is a biphasic rapid and sustained-release propranolol formulation similar to that described in WO 92/06680. Typically these materials melt upon heating, thereby allowing the use of conventional mixing and pumping technology for fluid filling.

|   |   | mg/capsule |
|---|---|---|
| A. | Sustained-Release Phase | |
|   | Propranolol | 40.0 |
|   | Oleic Acid BP | 102.1 |
|   | Colloidal silicon dioxide (Aerosil 200) | 8.2 |
|   | Polyoxyl-40-hydrogenated castor oil NF (Cremophor RH40) | 27.2 |
|   | Saturated polyglycolysed glycerides Ph.F. (Gelucire 50/02) | 94.5 |
| B. | Phase Barrier | |
|   | Saturated polyglycolysed glycerides Ph.F. (Gelucire 44/14) | 150.0 |
| C. | Rapid-Release Phase | |
|   | Propranolol base | 40.0 |
|   | Oleic acid BP | 110.0 |

A. Sustained-Release Phase

The oleic acid, Gelucire 50/02 and Cremophor were heated to 50° C.–55° C. until a clear solution was obtained. Propranolol base was added with stirring, while maintaining the temperature of the mix at 50° C. and continued until the propranolol base was fully dissolved. Finally Aerosil was added while stirring. A total of 272 mg of the formulation was filled into size 0 hard gelatin capsules while hot and then allowed to solidify with cooling.

B. Phase Barrier

The Gelucire 44/14 was heated until fully melted at 45° C.–55° C. and 150 mg filled over the sustained-release phase, previously filled into size 0 hard gelatin capsules, and allowed to solidify with cooling.

C. Rapid-Release Phase

Oleic acid was heated with stirring at 45° C.–50° C. Propranolol base was added and dissolved with stirring and allowed to cool. A total of 150 mg of the liquid rapid-release formulation was then filled over the phase barrier. The resulting capsules contained a solid sustained-release phase, solid phase separation barrier and liquid rapid-release phase. The capsules were then sealed by gelatin banding. Following gelatin banding, the capsules may be enteric-coated as described in WO 92/06680.

Example 2

Dissolution Studies With and Without Phase Barrier System

For evaluating the dispersion behaviour of the experimental formulations, a test-method was devised based upon the USP XXII dissolution test for tablets and capsules. The aim of the test was to subject the samples to an environment similar to that in the intestine. Dispersion in 5 hours was selected as a satisfactory total release time for the test samples. This was based on the understanding that lymphatic absorption occurs predominantly in the small intestine.

The dissolution apparatus as specified by the USP XXII (apparatus 2) was used with Sorensens phosphate buffer, pH 6.8 containing 0.2% sodium cholate and 0.1% sodium deoxycholate, equilibrated to 37° C. The total volume of buffer added to each dissolution vessel was 900 ml, with a paddle rotation speed of 70 rpm. The paddle height was adjusted so that the top edge of the blade was level with the surface of the liquid. The test sample was dropped into the dissolution medium and the rotation of the paddle started. The test sample was allowed to float freely at the liquid surface throughout the test. At each time-point., a 5 ml aliquot of the dissolution medium was removed and replaced with 5 ml of fresh buffer solution. Each 5 ml sample was initially filtered through 1.2 $\mu$M coarse filter and subsequent 1.2 $\mu$M fine filter. The absorbance for the filtered solution was then determined at 290 nm using a UV at 290 nm using a UV dissolution medium was calculated using a pre-determined calibration curve for propranolol.

A=Example 1 with phase barrier.

A=Example 1 without phase barrier.

TABLE 1

| | 30° C. Storage | | | | | |
|---|---|---|---|---|---|---|
| | % Propranolol Release | | | | | |
| Time | Initial | | 3 Months | | 7 Months | |
| (minutes) | A | B | A | B | A | B |
| 15 | 36 | 44 | 39 | 30 | 34 | 23 |
| 30 | 41 | 53 | 51 | 38 | 45 | 29 |
| 60 | 49 | 60 | 57 | 47 | 50 | 35 |
| 120 | 58 | 64 | 64 | 61 | 55 | 43 |
| 300 | 77 | 71 | 78 | 71 | 69 | 59 |

TABLE 2

| | 37° C. Storage | | | |
|---|---|---|---|---|
| | % Propranolol Release | | | |
| Time | Initial | | 1 Month | |
| (minutes) | A | B | A | B |
| 15 | 36 | 44 | 26 | 15 |
| 30 | 41 | 53 | 44 | 25 |
| 60 | 49 | 60 | 48 | 37 |
| 120 | 58 | 64 | 51 | 45 |
| 300 | 77 | 71 | 62 | 54 |

As is clear from the results shown in Tables 1 and 2 the presence of a barrier between the solid sustained release phase and the liquid phase improves considerably the amount of propranalol released, particularly from the sustained release phase. The effect of the barrier increases with the length of time for which the capsules are stored.

Example 3

Biphasic Propranolol Formulation with Solid Rapid-Release Phase

This is an example of a biphasic rapid and sustained-release propranolol formulation based on that described in WO-A-9206680, except that phase intermixing is prevented by having a solid rapid-release phase. The rapid-release phase is formulated as a solid, using Gelucire® 33/01, which melts on heating above 30° C. allowing (i) capsule filling to take place using conventional mixing and pumping technology, and (ii) enables rapid-release to take place at normal temperature.

|   |   | mg/capsule |
|---|---|---|
| A. | Sustained-Release Phase | 272.0 |
|   | As for Example I |   |
| B. | Solid Rapid-Release Phase |   |
|   | Propranolol base | 40.0 |
|   | Oleic acid B.P. | 110.0 |
|   | Saturated polyglycolysed glycerides Ph.F. (Gelucire ® 33/01) | 150.0 |

The modified rapid-release phase was manufactured by heating oleic acid at 45–50° C. with stirring. Propranolol base and Gelucire® 33/01 were added with stirring until completely dissolved. The molten rapid-release phase was maintained above 37° C. until filled into capsules already containing the solid sustained-release phase described in Example 1. A total of 300 mg of the modified sustained-release phase containing Gelucire® 33/01 was filled into size 0 hard gelatin capsules while hot and then allowed to solidify with cooling. The capsules were then sealed by gelatin banding. Following gelatin banding, the capsules may be enteric-coated as described in WO-A-9206680 and Burns et al, *International Journal of Pharmaceutics*, 110: 291–296 (1994).

Example 4

Dissolution Studies Using Solid Rapid-Release Phase System

The same dissolution method as described in Example 2 was used to evaluate capsules containing the biphasic rapid and sustained-release preparation described in Example 3.

TABLE 3

| | 25° C. Storage % Propranolol Release | | |
|---|---|---|---|
| Time (minutes) | Initial | 2 Months | 12 Months |
| 15 | 32 | 26 | 23 |
| 30 | 52 | 49 | 50 |
| 60 | 60 | 61 | 64 |
| 120 | 65 | 67 | 71 |
| 300 | 75 | 83 | 82 |

TABLE 4

| | 30° C. Storage % Propranolol Release | | | |
|---|---|---|---|---|
| Time (minutes) | Initial | 1 Month | 2 Months | 12 Months |
| 15 | 32 | 22 | 27 | 14 |
| 30 | 52 | 43 | 54 | 37 |
| 60 | 60 | 59 | 62 | 66 |
| 120 | 65 | 64 | 80 | 76 |
| 300 | 75 | 84 | 85 | 77 |

The results in Table 3 show that at 25° C. the dissolution profile of a biphasic formulation is maintained for at least 12 months. Table 4 shows that at 30° C., close to the melting point of the modified rapid-release phase containing Gelucire® 33/01, there is a small deterioration in initial release rate. However, the overall biphasic release characteristics of the formulation are maintained.

What is claimed is:

1. A pharmaceutical formulation which is a capsule, said capsule having a shell formed from a material selected from the group consisting of hard gelatin and starch, said capsule containing at least a first fill composition and a second fill composition different from the first fill composition, wherein the first and the second fill compositions are hydrophobic in nature, wherein said shell defines a single compartment and wherein said first and second fill compositions are prevented from mixing with one another by a third fill composition of a different material from that of the capsule shell, said third fill composition defining a physical barrier between said first and second fill compositions, and wherein the third fill composition is hydrophilic in nature.

2. The formulation as claimed in claim 1, wherein the physical barrier comprises a material having a melting point higher than 25° C.

3. The formulation as claimed in claim 2, wherein the physical barrier comprises a material having a melting point higher than 37° C.

4. The pharmaceutical formulation as claimed in claim 1, wherein the physical barrier comprises a glyceride.

5. The composition as claimed in claim 4, wherein the physical barrier material comprises a hydrogenated fatty acid ester or a mixture of esters.

6. The pharmaceutical formulation as claimed in claim 4, wherein the physical barrier comprises a di- or tri-glyceride, or a mixture of glycerides.

7. The formulation as claimed in claim 1, wherein either the first or the second fill composition comprises propanalol.

8. The formulation as claimed in claim 1, wherein both the first and the second fill compositions comprise propanalol.

9. The formulation as claimed in claim 1 comprising a first fill composition comprising a C12–C24 fatty acid and a pharmaceutically active agent, formulated for rapid release upon non-parenteral administration; and a second fill composition comprising a C12–C24 fatty acid and a pharmaceutically active agent formulated for sustained release of the active agent upon non-parenteral administration.

10. The formulation as claimed in claim 9, wherein the physical barrier is formed from a mixture of hydrogenated fatty acid esters which is hydrophilic in nature.

11. The pharmaceutical formulation as claimed in claim 9, wherein the physical barrier comprises a glyceride.

12. The pharmaceutical formulation as claimed in claim 11, wherein the physical barrier comprises a di- or tri-glyceride, or a mixture of glycerides.

13. The formulation as claimed in claim 9, wherein either the first or the second fill composition comprises propanalol.

14. The formulation as claimed in claim 9, wherein both the first and the second fill compositions comprise propanalol.

* * * * *